(12) United States Patent
Kintz

(10) Patent No.: US 10,426,661 B2
(45) Date of Patent: Oct. 1, 2019

(54) METHOD AND APPARATUS FOR LASER ASSISTED CATARACT SURGERY

(71) Applicant: Auris Health, Inc., Redwood City, CA (US)

(72) Inventor: Greg Kintz, Santa Cruz, CA (US)

(73) Assignee: Auris Health, Inc., Redwood City, CA (US)

( * ) Notice: Subject to any disclaimer, the term of this patent is extended or adjusted under 35 U.S.C. 154(b) by 590 days.

(21) Appl. No.: 14/458,042

(22) Filed: Aug. 12, 2014

(65) Prior Publication Data
US 2015/0051592 A1  Feb. 19, 2015

Related U.S. Application Data

(60) Provisional application No. 61/865,454, filed on Aug. 13, 2013.

(51) Int. Cl.
*A61F 9/007* (2006.01)
*A61F 9/008* (2006.01)

(52) U.S. Cl.
CPC .......... *A61F 9/00736* (2013.01); *A61F 9/008* (2013.01); *A61F 9/00825* (2013.01); *A61F 2009/0087* (2013.01); *A61F 2009/00887* (2013.01)

(58) Field of Classification Search
CPC .......................... A61B 2018/263; A61B 18/26
See application file for complete search history.

(56) References Cited

U.S. PATENT DOCUMENTS

| | | |
|---|---|---|
| 4,040,413 A | 8/1977 | Ohshiro |
| 4,198,960 A | 4/1980 | Utsugi |
| 4,470,407 A | 9/1984 | Hussein |
| 4,597,388 A | 7/1986 | Koziol et al. |
| 4,685,458 A | 8/1987 | Leckrone |
| 4,747,405 A | 5/1988 | Leckrone |
| 4,898,574 A | 2/1990 | Uchiyama et al. |
| 4,905,673 A | 3/1990 | Pimiskern |
| 4,983,165 A | 1/1991 | Loiterman |
| 5,029,574 A | 7/1991 | Shimamura et al. |

(Continued)

FOREIGN PATENT DOCUMENTS

| | | |
|---|---|---|
| JP | H09224951 A | 9/1997 |
| WO | WO 92/14411 A1 | 9/1992 |

(Continued)

OTHER PUBLICATIONS

U.S. Appl. No. 14/578,082, filed Dec. 19, 2014, Alvarez et al.

(Continued)

*Primary Examiner* — Scott Luan
(74) *Attorney, Agent, or Firm* — Knobbe, Martens, Olson & Bear, LLP

(57) ABSTRACT

Devices and methods for use in laser-assisted surgery, particularly cataract surgery. Specifically, the use of an optical fiber with a proximal and distal end, wherein the distal end has a non-orthogonal angle with the diameter of the optical fiber, to create an off-axis steam bubble for cutting and removing tissue in an operative region. Where the optical fiber is bent, rotating the fiber creates a circular cutting path for the steam bubble, allowing access to tissues that may normally be blocked by obstructions and obstacles.

20 Claims, 15 Drawing Sheets

(56) References Cited

U.S. PATENT DOCUMENTS

| | | |
|---|---|---|
| 5,085,659 A | 2/1992 | Rydell |
| 5,308,323 A | 5/1994 | Sogawa et al. |
| 5,325,848 A | 7/1994 | Adams et al. |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,425,735 A | 6/1995 | Rosen et al. |
| 5,431,649 A | 7/1995 | Mulier et al. |
| 5,441,485 A | 8/1995 | Peters |
| 5,450,843 A | 9/1995 | Moll et al. |
| 5,472,406 A | 12/1995 | De La Torre et al. |
| 5,472,426 A | 12/1995 | Bonati et al. |
| 5,501,667 A | 3/1996 | Verduin, Jr. |
| 5,520,684 A | 5/1996 | Imran |
| 5,562,648 A | 10/1996 | Peterson |
| 5,562,678 A | 10/1996 | Booker |
| 5,572,999 A | 11/1996 | Funda et al. |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,662,590 A | 9/1997 | De La Torre et al. |
| 5,695,461 A | 12/1997 | Schaible |
| 5,695,500 A | 12/1997 | Taylor et al. |
| 5,710,870 A | 1/1998 | Ohm |
| 5,716,325 A | 2/1998 | Bonutti |
| 5,788,667 A | 8/1998 | Stoller |
| 5,810,770 A | 9/1998 | Chin et al. |
| 5,924,175 A | 7/1999 | Lippitt |
| 5,989,230 A | 11/1999 | Frassica |
| 6,033,371 A | 3/2000 | Tone et al. |
| 6,071,281 A | 6/2000 | Burnside et al. |
| 6,093,157 A | 7/2000 | Chandrasekaran |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,183,435 B1 | 6/2001 | Bumbalough et al. |
| 6,326,616 B1 | 12/2001 | Andrien et al. |
| 6,398,792 B1 | 6/2002 | O'Connor |
| 6,405,078 B1 | 6/2002 | Moaddeb et al. |
| 6,406,486 B1 | 6/2002 | De La Torre et al. |
| 6,436,107 B1 | 8/2002 | Wang et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,554,793 B1 | 4/2003 | Pauker et al. |
| 6,577,891 B1 | 6/2003 | Jaross et al. |
| 6,638,246 B1 | 10/2003 | Naimark et al. |
| 6,671,581 B2 | 12/2003 | Niemeyer et al. |
| 6,676,668 B2 | 1/2004 | Mercereau et al. |
| 6,706,050 B1 | 3/2004 | Giannadakis |
| 6,736,784 B1 | 5/2004 | Menne et al. |
| 6,763,259 B1 | 7/2004 | Hauger et al. |
| 7,087,061 B2 | 8/2006 | Chernenko et al. |
| 7,282,055 B2 | 10/2007 | Tsuruta |
| 7,344,528 B1 | 3/2008 | Tu et al. |
| 7,351,193 B2 | 4/2008 | Forman et al. |
| 7,559,934 B2 | 7/2009 | Teague et al. |
| 7,725,214 B2 | 5/2010 | Diolaiti |
| 7,883,475 B2 | 2/2011 | Dupont et al. |
| 7,963,911 B2 | 6/2011 | Turliuc |
| 7,967,799 B2 | 6/2011 | Boukhny |
| 8,038,598 B2 | 10/2011 | Khachi |
| 8,049,873 B2 | 11/2011 | Hauger et al. |
| 8,092,397 B2 | 1/2012 | Wallace et al. |
| 8,187,173 B2 | 5/2012 | Miyoshi |
| 8,224,484 B2 | 7/2012 | Swarup et al. |
| 8,257,303 B2 | 9/2012 | Moll et al. |
| 8,414,564 B2 | 4/2013 | Goldshleger et al. |
| 8,518,024 B2 | 8/2013 | Williams et al. |
| 8,523,762 B2 | 9/2013 | Miyamoto et al. |
| 8,945,163 B2 | 2/2015 | Voegele et al. |
| 8,956,280 B2 | 2/2015 | Eversull et al. |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 10,016,900 B1 | 7/2018 | Meyer et al. |
| 10,022,192 B1 | 7/2018 | Ummalaneni |
| 2002/0019644 A1 | 2/2002 | Hastings |
| 2003/0040681 A1 | 2/2003 | Ng et al. |
| 2003/0109889 A1 | 6/2003 | Mercereau |
| 2004/0030349 A1 | 2/2004 | Boukhny |
| 2004/0135733 A1 | 7/2004 | Chou et al. |
| 2004/0143253 A1 | 7/2004 | Vanney |
| 2004/0158261 A1 | 8/2004 | Vu |
| 2004/0186349 A1 | 9/2004 | Ewers |
| 2004/0210116 A1 | 10/2004 | Nakao |
| 2005/0070844 A1 | 3/2005 | Chow et al. |
| 2005/0159645 A1 | 7/2005 | Bertolero |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2006/0229598 A1 | 10/2006 | Shadduck |
| 2007/0016164 A1 | 1/2007 | Dudney et al. |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135763 A1 | 6/2007 | Musbach et al. |
| 2007/0135803 A1 | 6/2007 | Belson |
| 2007/0213668 A1 | 9/2007 | Spitz |
| 2007/0250111 A1 | 10/2007 | Lu |
| 2007/0299427 A1 | 12/2007 | Yeung et al. |
| 2008/0033467 A1 | 2/2008 | Miyamoto et al. |
| 2008/0065109 A1 | 3/2008 | Larkin |
| 2008/0097293 A1 | 4/2008 | Chin et al. |
| 2008/0114341 A1 | 5/2008 | Thyzel |
| 2008/0125698 A1 | 5/2008 | Greg et al. |
| 2008/0177285 A1 | 7/2008 | Brock et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0036900 A1 | 2/2009 | Moll |
| 2009/0082634 A1 | 3/2009 | Kathrani et al. |
| 2009/0105723 A1 | 4/2009 | Dillinger |
| 2009/0161827 A1 | 6/2009 | Gertner et al. |
| 2009/0171271 A1 | 7/2009 | Webster et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0270760 A1 | 10/2009 | Leimbach et al. |
| 2009/0287188 A1 | 11/2009 | Golden et al. |
| 2009/0312768 A1 | 12/2009 | Hawkins et al. |
| 2009/0326322 A1 | 12/2009 | Diolaiti |
| 2010/0036294 A1 | 2/2010 | Mantell et al. |
| 2010/0073150 A1 | 3/2010 | Olson et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2011/0009779 A1 | 1/2011 | Romano et al. |
| 2011/0015483 A1 | 1/2011 | Barbagli |

(56) References Cited

U.S. PATENT DOCUMENTS

| | | |
|---|---|---|
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0071541 A1 | 3/2011 | Prisco et al. |
| 2011/0071543 A1 | 3/2011 | Prisco et al. |
| 2011/0106102 A1 | 5/2011 | Balicki et al. |
| 2011/0125165 A1 | 5/2011 | Simaan et al. |
| 2011/0160713 A1* | 6/2011 | Neuberger ............ A61B 18/22 606/15 |
| 2011/0213362 A1 | 9/2011 | Cunningham |
| 2011/0224660 A1* | 9/2011 | Neuberger ............ A61B 18/22 606/15 |
| 2011/0257641 A1* | 10/2011 | Hastings ............... A61B 18/24 606/15 |
| 2011/0306836 A1 | 12/2011 | Ohline et al. |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0172786 A1 | 7/2012 | Mackool |
| 2012/0232342 A1 | 9/2012 | Reydel |
| 2012/0253332 A1 | 10/2012 | Moll |
| 2012/0259320 A1 | 10/2012 | Loesel et al. |
| 2012/0283747 A1 | 11/2012 | Popovic |
| 2012/0296318 A1 | 11/2012 | Wellhofer et al. |
| 2013/0006144 A1 | 1/2013 | Clancy |
| 2013/0066136 A1 | 3/2013 | Palese et al. |
| 2013/0072787 A1 | 3/2013 | Wallace et al. |
| 2013/0085442 A1 | 4/2013 | Shtul et al. |
| 2013/0085486 A1* | 4/2013 | Boutoussov ........... A61B 18/22 606/16 |
| 2013/0096574 A1 | 4/2013 | Kang et al. |
| 2013/0110042 A1 | 5/2013 | Humphreys |
| 2013/0116714 A1 | 5/2013 | Adams et al. |
| 2013/0116716 A1 | 5/2013 | Bahls et al. |
| 2013/0144116 A1 | 6/2013 | Cooper et al. |
| 2013/0190796 A1 | 7/2013 | Tilson et al. |
| 2013/0225997 A1 | 8/2013 | Dillard et al. |
| 2013/0253267 A1 | 9/2013 | Collins |
| 2013/0303876 A1 | 11/2013 | Gelfand et al. |
| 2013/0310819 A1* | 11/2013 | Neuberger ............ A61B 18/22 606/10 |
| 2014/0012276 A1 | 1/2014 | Alvarez |
| 2014/0039681 A1 | 2/2014 | Bowling |
| 2014/0051985 A1 | 2/2014 | Fan |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0275956 A1 | 9/2014 | Fan |
| 2014/0276594 A1 | 9/2014 | Tanner et al. |
| 2014/0276723 A1 | 9/2014 | Parihar |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0164522 A1 | 6/2015 | Budiman |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0201917 A1 | 7/2015 | Snow |
| 2015/0202085 A1 | 7/2015 | Lemonis |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0030073 A1 | 2/2016 | Lsakov |
| 2016/0045208 A1 | 2/2016 | Ciulla |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0331358 A1 | 11/2016 | Gordon |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0065364 A1 | 3/2017 | Schuh et al. |
| 2017/0065365 A1 | 3/2017 | Schuh |
| 2017/0095234 A1 | 4/2017 | Prisco et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055583 A1 | 3/2018 | Schuh et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |

FOREIGN PATENT DOCUMENTS

| | | |
|---|---|---|
| WO | WO 03/096871 A2 | 11/2003 |
| WO | WO 2004/105849 A1 | 12/2004 |
| WO | WO 2011/161218 A1 | 12/2011 |
| WO | WO 13/107468 | 7/2013 |
| WO | WO 13/130895 | 9/2013 |
| WO | WO 17/114655 | 7/2017 |

OTHER PUBLICATIONS

U.S. Appl. No. 14/583,021, filed Dec. 24, 2014, Romo et al.
International search report and written opinion dated Jan. 27, 2015 for PCT Application No. US2014/062284.
U.S. Appl. No. 14/196,953, filed Mar. 4, 2014, Alvarez et al.
U.S. Appl. No. 14/201,610, filed Mar. 7, 2014, Romo.
U.S. Appl. No. 14/301,871, filed Jun. 11, 2014, Alvarez et al.
U.S. Appl. No. 14/479,095, filed Sep. 5, 2014, Romo et al.
U.S. Appl. No. 14/523,760, filed Oct. 24, 2014, Alvarez et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.

(56) References Cited

OTHER PUBLICATIONS

Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
U.S. Appl. No. 14/542,373, filed Nov. 14, 2014, Romo et al.
U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
Office action dated Oct. 7, 2014 for U.S. Appl. No. 13/711,440.
European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.

\* cited by examiner

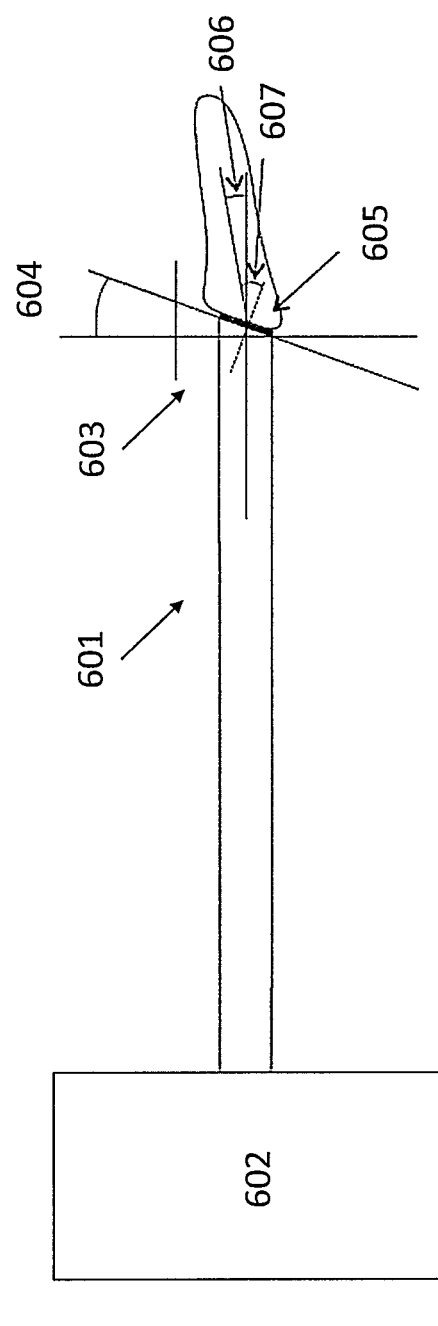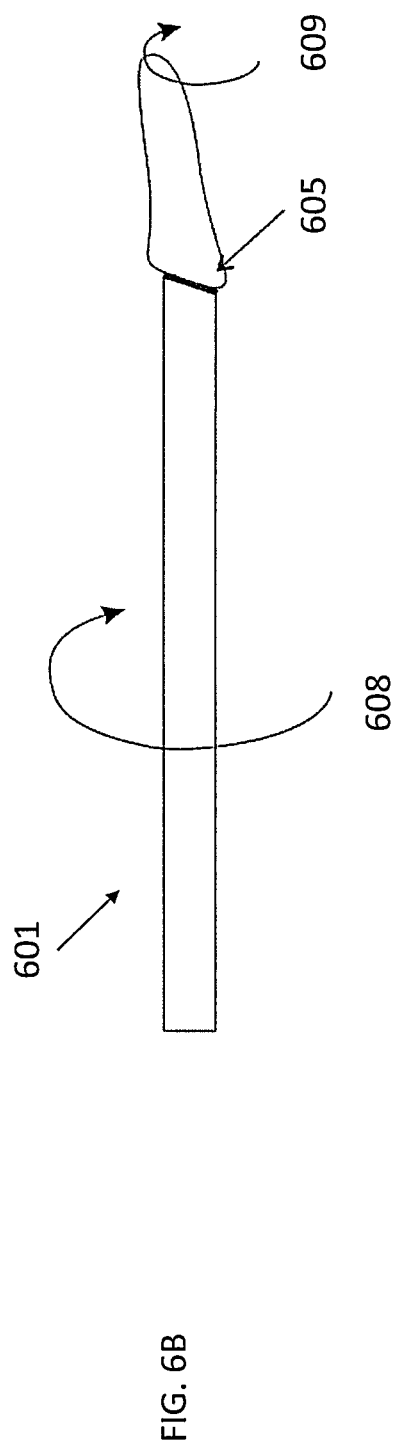
FIG. 6A
FIG. 6B

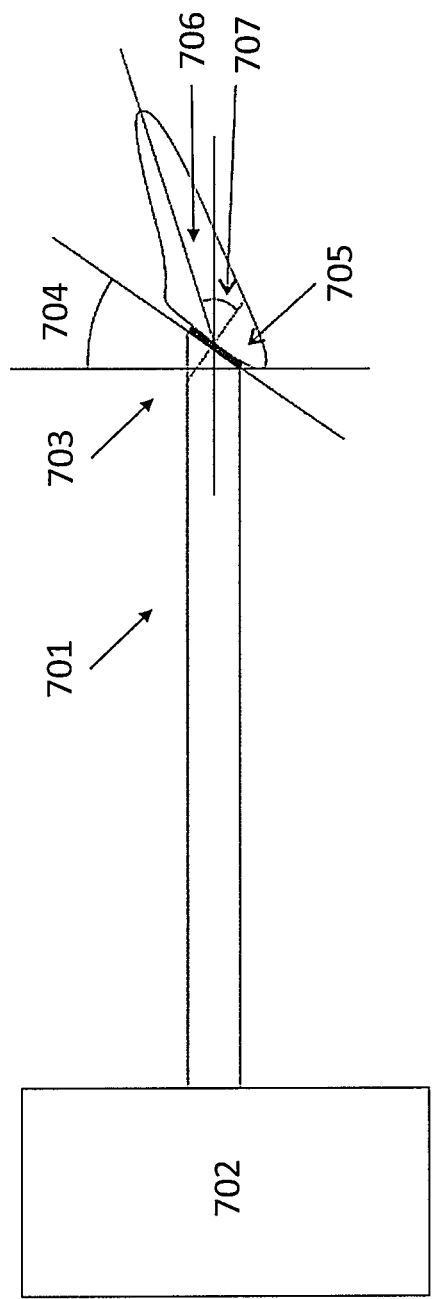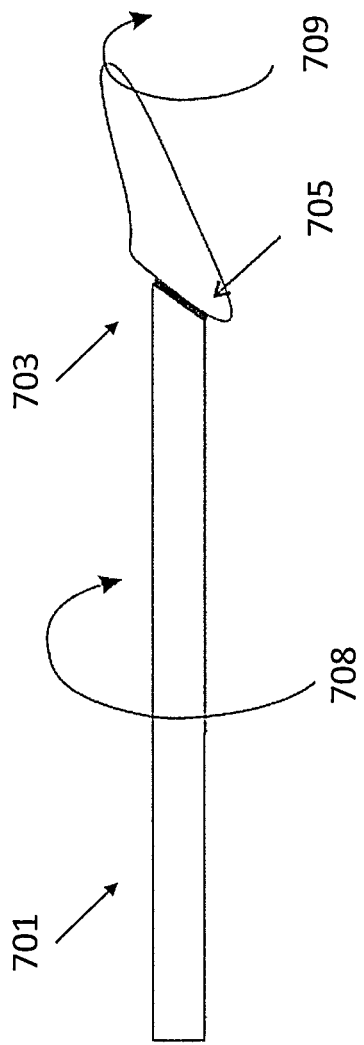
FIG. 7A
FIG. 7B

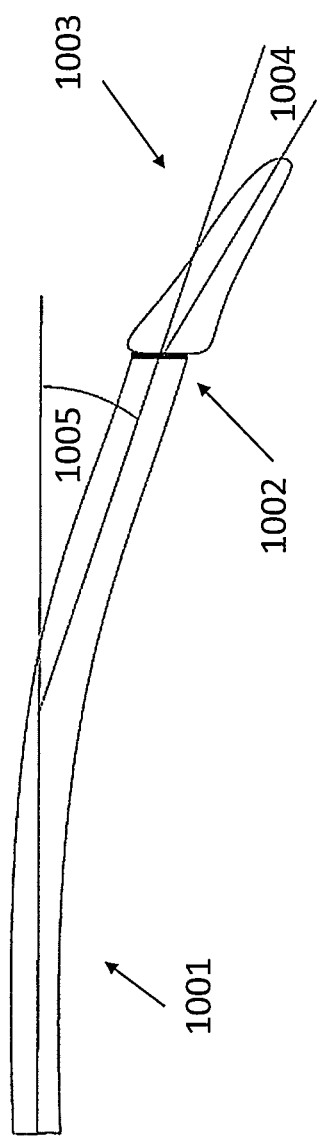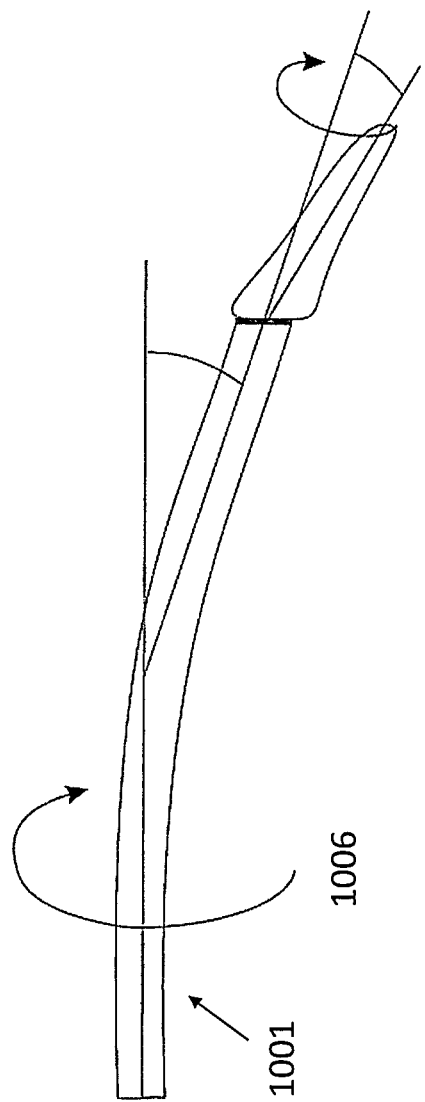
FIG. 10A
FIG. 10B

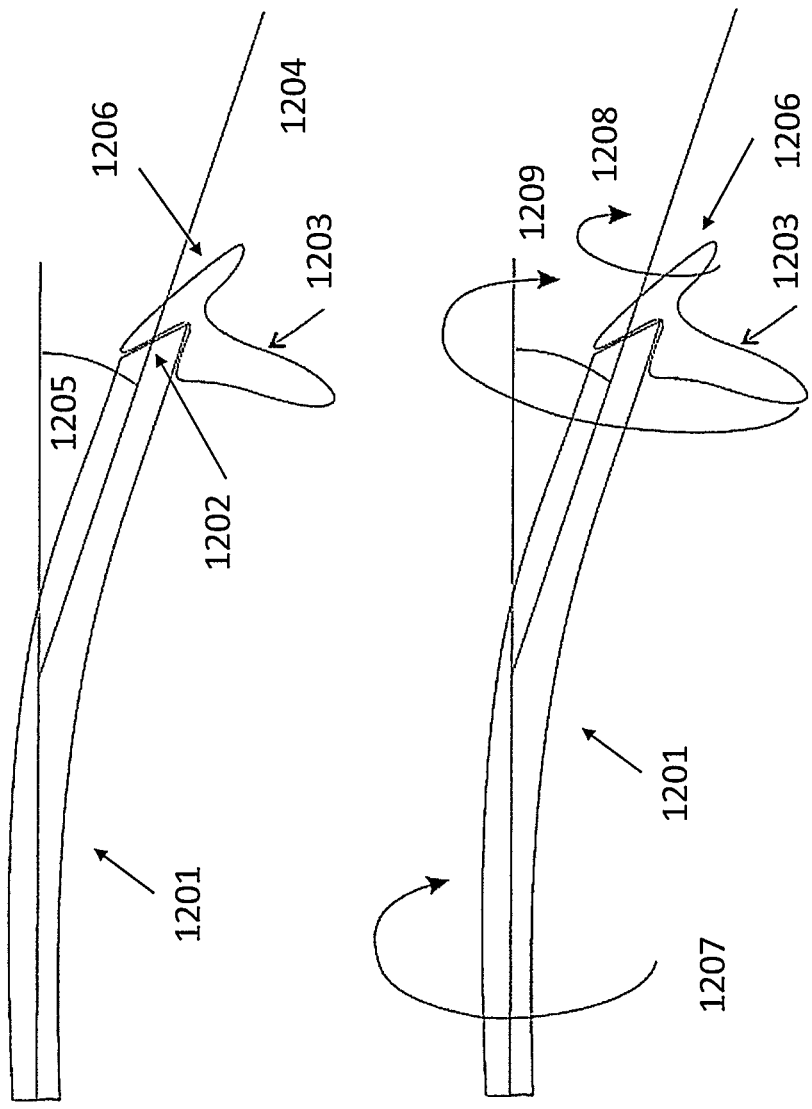

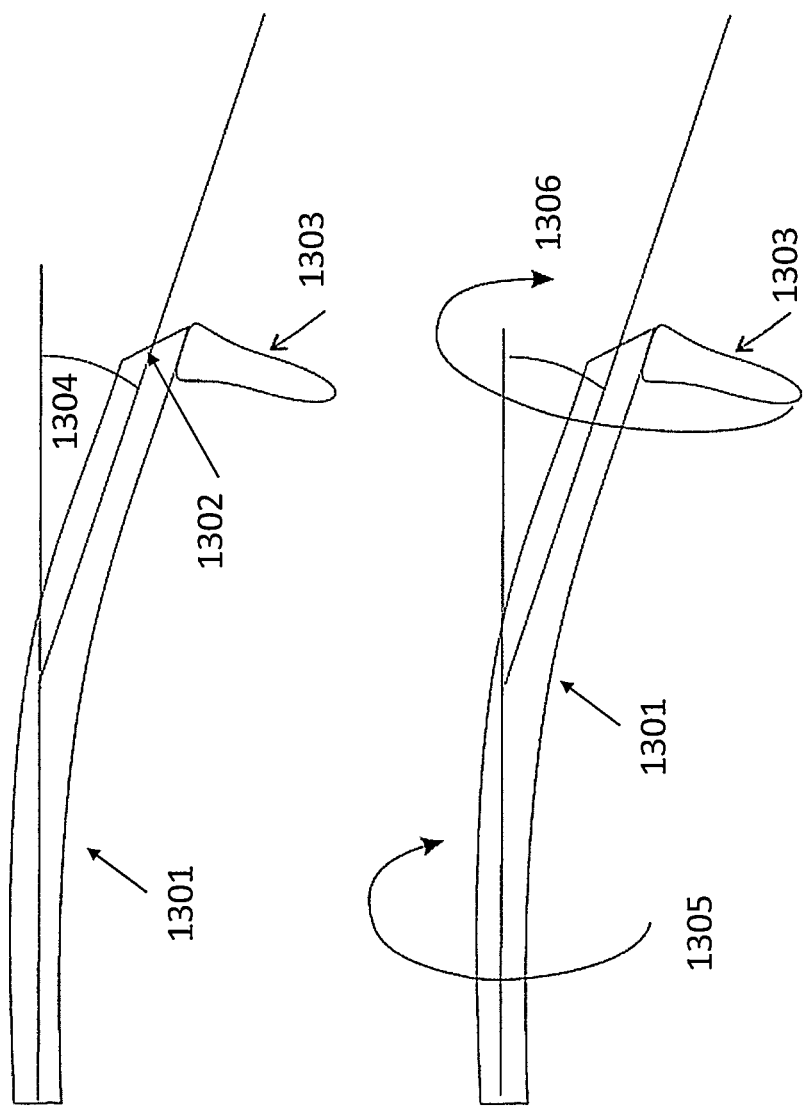

METHOD AND APPARATUS FOR LASER ASSISTED CATARACT SURGERY

CROSS-REFERENCE TO RELATED APPLICATIONS

This application 8 claims benefit of U.S. Provisional Application Ser. No. 61/865,454, filed Aug. 13, 2013, the entire contents of which is incorporated herein by reference.

FIELD OF THE INVENTION

The field of the present application pertains to medical devices. More particularly, the field of the invention pertains to an apparatus, system, and method for laser assisted cataract surgery.

BACKGROUND OF THE INVENTION

A "cataract" is a clouding of the lens in the eye that affects vision. Most people develop cataracts due to aging. The condition is not uncommon; it is estimated more than half of all Americans will either have a cataract or have had cataract surgery by age 80.

FIG. 1 is a diagram of the human eye, included for background. The major features of the eye 100 comprise the cornea 101, the anterior chamber 102, the iris 103, the lens capsule 104, the lens 105, the vitreous 106, the retina 107, and the sclera 108. The lens capsule 104 has an anterior surface 109 bordering the anterior chamber 102 and a posterior surface 110 bordering the vitreous 106. Most relevant to cataracts, the lens 105 within the lens capsule 104 is comprised of a nucleus 111 and cortex 112.

As shown in FIG. 1, the lens 105 within the eye 100 lies behind the iris 103. In principle, it focuses light onto the retina 107 at the back of the eye 100 where an image is recorded. The lens 105 also adjusts the focus of the eye 100, allowing it to focus on objects both near and far.

The lens 105 contains protein that is precisely arranged to keep the lens 105 clear and allow light to pass through it. As the eye ages, the protein in the lens 105 may clump together to form a "cataract". Over time, the cataract may grow larger and obscure a larger portion of the lens 105, making it harder for one to see.

Age-related cataracts affect vision in two ways. The clumps of protein forming the cataract may reduce the sharpness of the image reaching the retina 107. The clouding may become severe enough to cause blurred vision. The lens 105 may slowly change to a yellowish/brownish tint. As the lens 105 ages, objects that once appeared clear may gradually appear to have a brownish tint. While the amount of tinting may be small at first, increased tinting over time may make it more difficult to read and perform other routine activities.

Surgery is currently the only real treatment for cataracts. Each year, ophthalmologists in the United States perform over three million cataract surgeries. The vast majority of cataracts are removed using a procedure called extracapsular cataract extraction (ECCE). ECCE traditionally comprises of several steps. Incisions must first be made to the cornea 101 in order to introduce surgical instruments into the anterior chamber 102. Through the incisions in the cornea 101 and the space of the anterior chamber 102, the surgeon may remove the anterior face of the lens capsule 109 in order to access the lens underneath 105. This phase of the surgery, known as capsulorhexis, is often the most difficult procedure in ECCE.

Having gained access to the lens through capsulorhexis, a small amount of fluid may be injected into the exposed lens capsule 104 to improve access and maneuverability of the lens 105. This phase of the surgery is known as hydrodissection to the skilled artisan.

After loosening the lens, it must be extracted. Traditionally, the lens is manually extracted through a large (usually 10-12 mm) incision made in the cornea 101 or sclera 108. Modern ECCE is usually performed using a micro surgical technique called phacoemulsification, whereby the cataract is emulsified with an ultrasonic handpiece and then suctioned out of the eye through incisions in the cornea 101.

A phacoemulsification tool may be an ultrasonic handpiece with a titanium or steel needle. The tip of the needle may vibrate at an ultrasonic frequency to sculpt and emulsify the cataract while a pump aspirates particles through the tip. In some circumstances, a second fine steel instrument called a "chopper" may be used to access the cataract from a side port to help with "chopping" the nucleus 111 into smaller pieces. Once broken into numerous pieces, each piece of the cataract is emulsified and aspirated out of the eye 100 with suction.

As the nucleus 111 often contains the hardest portion of the cataract, emulsification of the nucleus 111 makes it easier to aspirate the particles. In contrast, the softer outer material from the lens cortex 112 may be removed using only aspiration. After removing the lens material from the eye 100, an intraocular lens implant (IOL) may be placed into the remaining lens capsule 104 to complete the procedure.

One variation on phacoemulsification is sculpting and emulsifying the lens 105 using lasers rather than ultrasonic energy. In particular, femtosecond laser-based cataract surgery is rapidly emerging as a potential technology that allows for improved cornea incision formation and fragmentation of the cataract.

Phacoemulsification and laser-based emulsification, however, still have their shortcomings. Phacoemulsification requires the use of tools that propagate ultrasound energy along the length of the tool, from a proximal transducer to a distal tip. The propagation leads to the transmission of ultrasound energy along the tool to other tissues proximal to the eye 100. Ultrasound tools also generate more heat than would be desirable for a procedure in the eye 100. In addition, the mechanical requirements of propagating the ultrasound wave along the length of the tool often make it rigid and difficult to steer around corners or bends.

Laser-based tools have their own drawbacks. Presently, manually controlled lasers require careful, precise movement since they can easily generate unwanted heat in the eye 100. Laser fibers in the tool are also fragile, and thus easily damaged when attempting to navigate tight corners. Both limitations increase surgery time and raise safety concerns.

An alternative to conventional laser systems, femtosecond laser systems have their advantages and drawbacks as well. Femtosecond laser systems may be used to create entry sites through the cornea 101 and sclera 108 into the eye 100, as well as to remove the anterior face of the capsule 104. Femtosecond laser energy may be focused within the lens nucleus 111 itself, and used to "pre-chop" the lens nucleus 111 into a number of pieces that can then be easily removed with aspiration. Femtosecond lasers, however, can only fragment the central portion of the lens 105 because the iris 103 blocks the peripheral portion of the lens 105. Thus, use of another emulsification technology—ultrasound or conventional laser—is still necessary to fracture and remove the peripheral portion of the cataract in lens 105, extending total procedure time. Furthermore, femtosecond laser systems are also expensive and costly to operate and maintain.

As an alternative to a purely laser-based emulsification, certain systems may use the lasers to generate steam bubbles to create shockwaves to break up the cataract material during emulsification.

FIG. 2 is a diagram of a multimode optical fiber 200 with a flat tip at the distal end 201, included for illustration purposes. At the output of the distal end 201, all laser energy originating from laser source 203, and carried through optical fiber 200, is absorbed at the surface of fiber 200. If the laser energy is high enough, the surrounding water may vaporize and form a steam bubble 202. If the laser continues to output energy, the steam bubble 202 may grow into a cylindrical shape. A cylindrically-shaped steam bubble only occurs when the absorption depth in the water is relatively short; light energy with a wavelength near 3 µm can produce a cylindrically shaped steam bubble while light energy near 2 µm does not. The cylindrically-shaped steam bubble 202 produces a mechanical action that can cut or disrupt tissue.

FIG. 3 is a diagram of a multimode optical fiber 300 with a tapered (cone shaped) tip at the distal end 301, included for illustration purposes. At the output of the distal end 301 of optical fiber 300, all the laser energy may be absorbed at the surface of the cone shaped fiber. If the laser energy is high enough, the water vaporizes and forms steam bubble 302. If the laser continues to output energy, then the steam bubble can grow into a spherically-shaped steam bubble. The dynamics of steam bubble generation can be found in "Effect of microsecond pulse length and tip shape on explosive bubble formation of 2.78 µm Er,Cr;YSGG and 2.94 µm Er:YAG laser", Paper 8221-12, Proceedings of SPIE, Volume 8221 (Monday 23 Jan. 2013).

In both FIGS. 2 and 3, the steam bubbles generated by the optical fibers are collinear with the optical fiber. Being collinear, the orientation of the steam bubbles relative to the optical fibers create problems in certain applications. For example, during capsulorhexis, where the anterior portion of the lens capsule is removed, the orientation of the steam bubble presents a challenge because the tools are oriented at a steep angle to the lens capsule through incisions at the edge of the cornea.

Therefore, it would be beneficial to have a new method, apparatus, and system for using steam bubbles that are not collinear with the neutral axis of the optical fiber.

SUMMARY OF THE INVENTION

In general, the present invention provides a device and method for laser assisted cataract surgery using laser energy emitted by optical fibers to create steam bubbles. In one aspect, the present invention provides for a surgical device comprising an optical fiber having a proximal end and distal end, wherein the optical fiber is configured to generate a steam bubble from light energy conveyed out the distal end of the fiber, the proximal end is operatively connected to a light source, and the distal end comprises a tip with a non-orthogonal tilted edge across the diameter of the fiber.

A related device further comprises a tube that encloses the optical fiber. In some embodiments, the tube is pre-bent at a predetermined angle. In some embodiments, an angle of the tilted edge exceeds 45 degrees. In some embodiments, an angle of the tilted edge does not exceed 45 degrees. In some embodiments, the angle of the tilted edge exceeds 7 degrees but not 45 degrees. In some embodiments, the optical fiber is further configured to generate a second steam bubble from the application of laser energy.

In another aspect, the present invention provides for a method that comprises transmitting light energy through an optical fiber, generating a steam bubble; and directing the steam bubble to an operative region of a patient, wherein the optical fiber has a proximal end and a distal end, the optical fiber being configured to generate the steam bubble from light energy conveyed out the distal end of the fiber, the proximal end being operatively connected to a light source, and the distal end comprising a tip with a non-orthogonal tilted edge across the diameter of the fiber.

In related embodiments, the optical fiber is enclosed within a tube. In some embodiments, the tube is pre-bent at a predetermined angle. In some embodiments, the method further comprises axially rotating the tube to generate a circular cutting path for the steam bubble. In some embodiments, axially rotating the optical fiber to generate a circular cutting path for the steam bubble. In some embodiments, an angle of the tilted edge exceeds 45 degrees. In some embodiments, an angle of the tilted edge does not exceed 45 degrees. In some embodiments, the angle of the tilted edge exceeds 7 degrees but not 45 degrees.

BRIEF DESCRIPTION OF THE DRAWINGS

The invention will be described, by way of example, and with reference to the accompanying diagrammatic drawings, in which:

FIGS. 6A-6B illustrate an optical fiber coupled to a laser source where a steam bubble may be deflected from the axis of the fiber by incorporating a fiber with tilted end and a laser source with high water absorption, in accordance with an embodiment of the present invention;

FIGS. 7A-7B illustrate an optical fiber coupled to a laser source where a steam bubble may be deflected from the axis of the fiber by incorporating a fiber with a tilted end at 35 degrees, in accordance with an embodiment of the present invention;

FIGS. 10A-10B illustrate an embodiment of the present invention where the steam bubble is deflected from the axis of the fiber by incorporating a laser source with high water absorption, a bent optical fiber, and a tilted tip;

FIGS. 12A-12B illustrate an embodiment of the present invention where the steam bubble is deflected from the axis of the fiber by incorporating a laser source with high water absorption, a bent optical fiber, and a tilted end at the fiber; and FIGS. 13A-13B illustrate an embodiment of the present invention where the steam bubble only exits from the side from a bent optical fiber with a tilted end at the fiber.

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

As is known in the art, the conveyance of light energy at an interface of two materials is affected by the angle of incidence of the light energy, the index of refraction of the two substances, and the critical angle of the interface. When light is travelling from a high index of refraction material to a low index of refraction material and the angle of incidence is below the critical angle, the light largely passes from the high index of refraction to a low index of refraction material. When light is travelling from a high index of refraction material to a low index of refraction material and the angle of incidence is above the critical angle, the light reflects off the interface. If some of the light is greater than the critical angle, the light will exit the fiber from the side of the fiber. If all of the light in the fiber hits the titled end at greater than the critical angle, then all of the light will exit the side of the fiber.

Higher index materials have correspondingly smaller critical angles. For example, for light coming from fused silica into air, the critical angle is 44.6 degrees. In contrast, the critical angle in water is lower.

Figure 1:
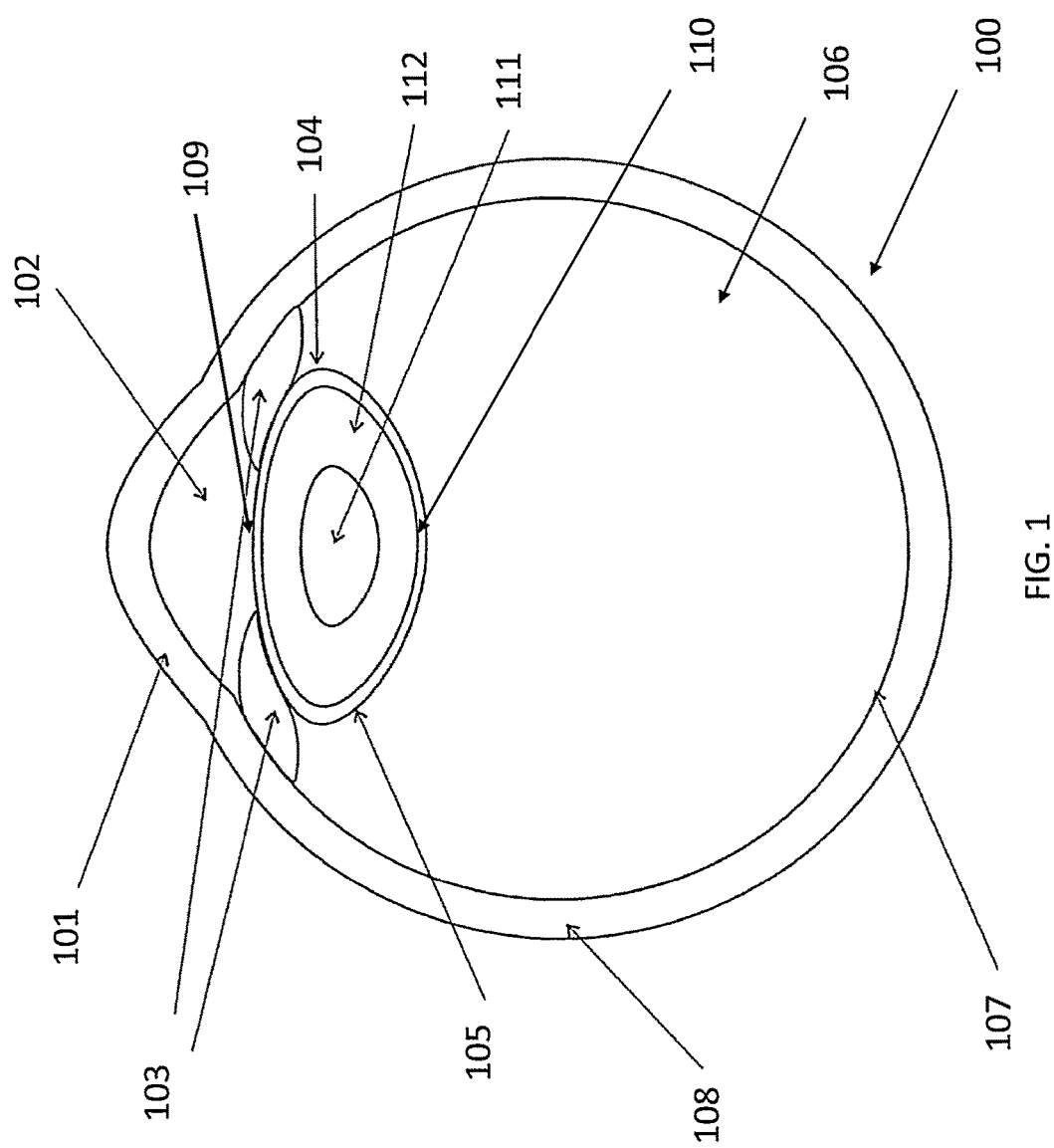
FIG. 1 illustrates the portions of the human eye, included for background.
Figure 2:
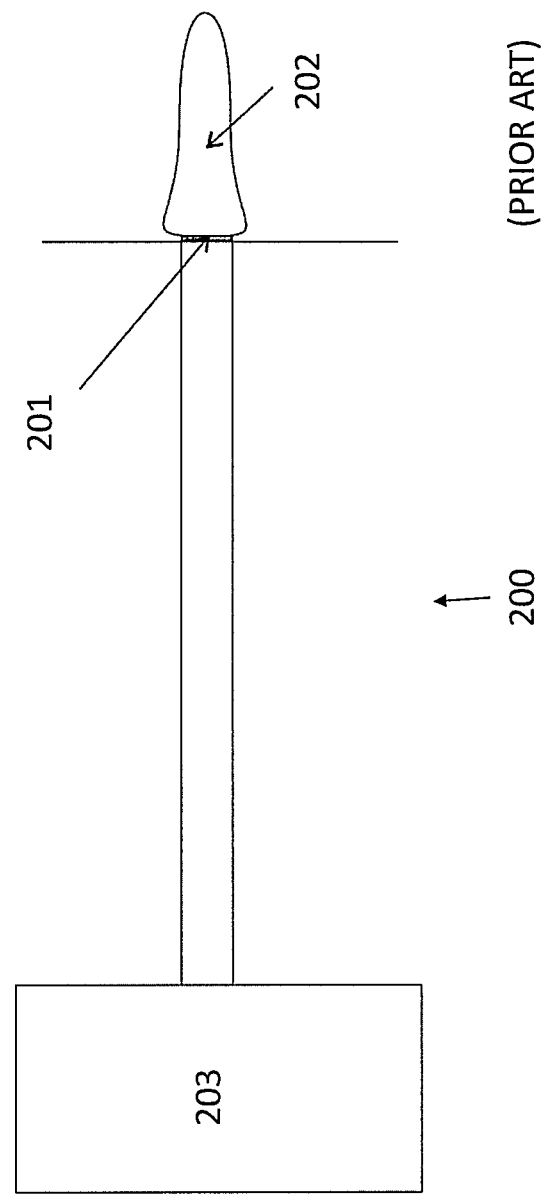
FIG. 2 illustrates a multimode optical fiber with a flat tip at the distal end, included for illustration purposes.
Figure 3:
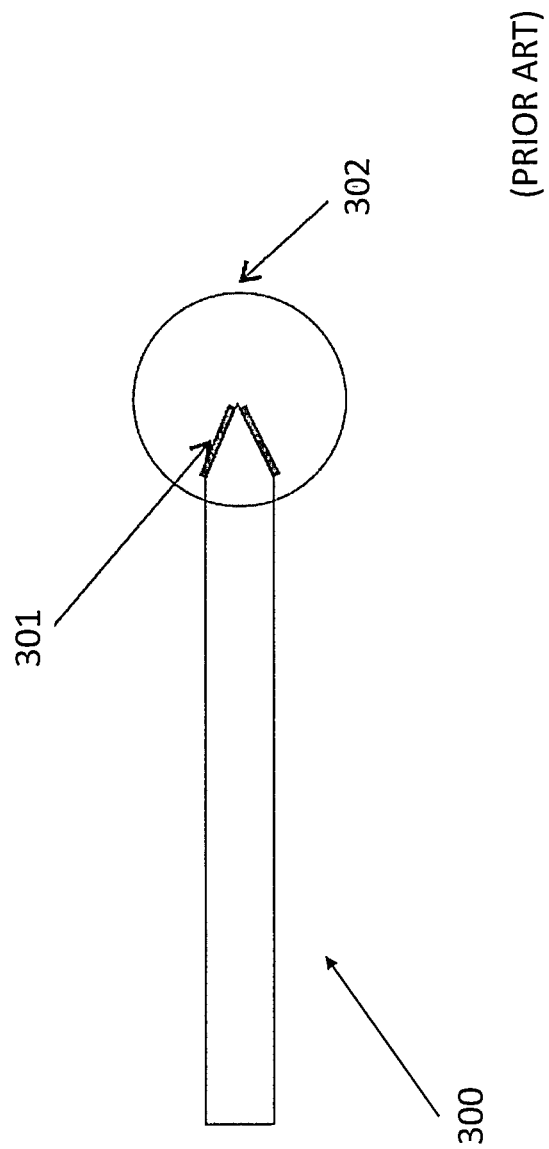
FIG. 3 illustrates a multimode optical fiber with a tapered (cone shaped) tip at the distal end, included for illustration purposes.
Figure 4A:
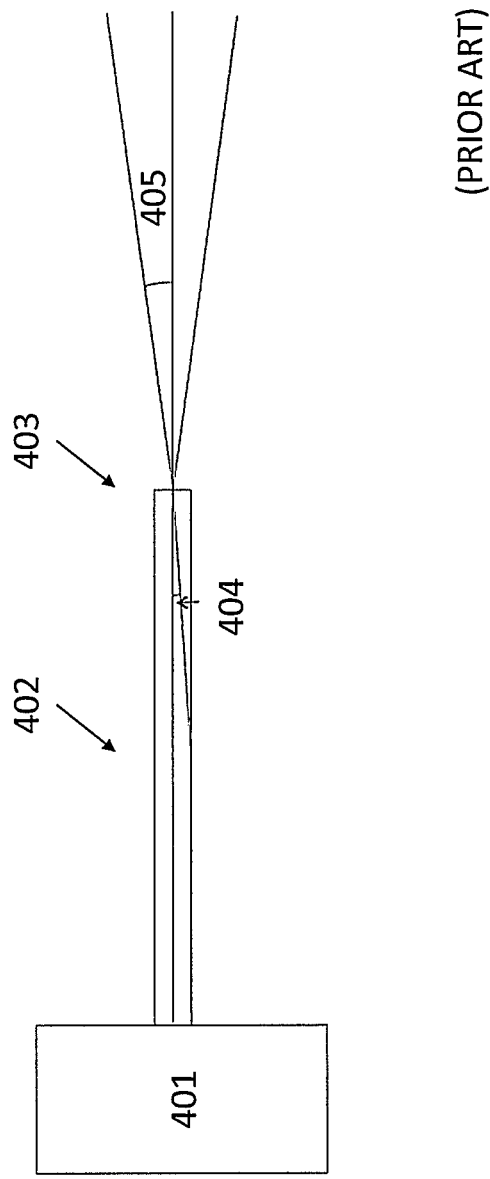
FIGS. 4A-4B illustrate an optical fiber coupled to a laser source consistent with the prior art, included for explanative purposes.

FIG. 4 illustrates an optical fiber 402 coupled to a laser source 401 consistent with the prior art, included for explanative purposes. As shown in FIG. 4A specifically, the conveyance of laser energy into and out of the optical fiber 402 contemplates two acceptance angles: (a) the angle required for light traveling down a multimode optical fiber to remain in the fiber, and (b) the angle of the laser energy exiting the end of the fiber. Thus, laser energy traveling at angles greater than the fiber's acceptance angle 404 exits the fiber 402 prior to reaching the distal end 403. When the laser energy exits the optical fiber 402, the acceptance angle is represented by 405.

Figure 4B:
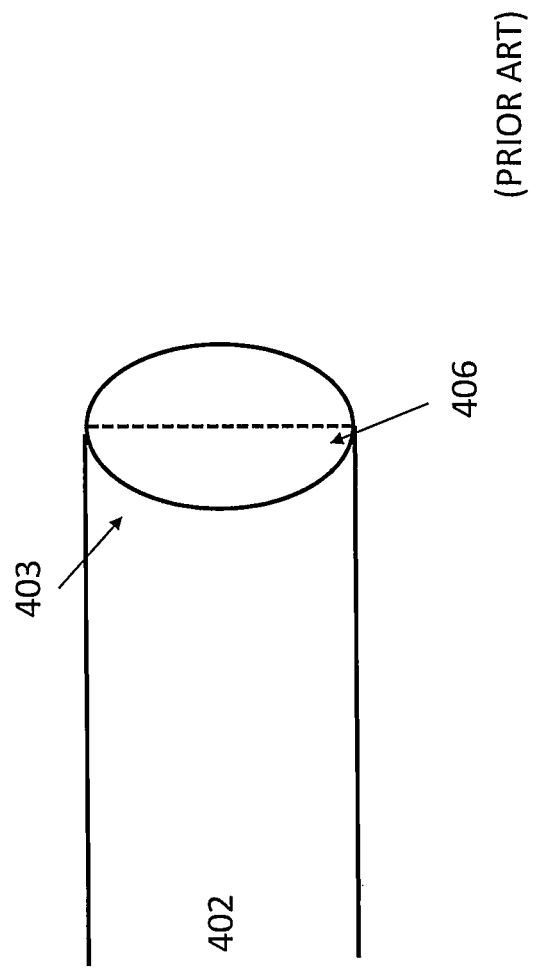

FIG. 4B illustrates the distal end 403 of optical fiber 402 consistent with the prior art, included for explanation purposes. As shown in FIG. 4B, the tip of the distal end 403 is formed by an orthogonal cut across the diameter of the optical fiber 402. The cut forms an approximately a right angle, i.e., ninety degrees, with the length of the optical fiber 402. In other words, the plane formed at the tip of distal end 403 is approximately orthogonal to the longitudinal axis of the optical fiber 402.

In some applications including the cutting of membranes, it is desirable to have the steam bubble perpendicular to the surface of the membrane. Thus, in some embodiments, the ability to add steam bubble deflection to the fiber can allow for sharper bends of the steam bubble relative to the membrane surface since fibers have a finite bending radius.

Figure 5A:
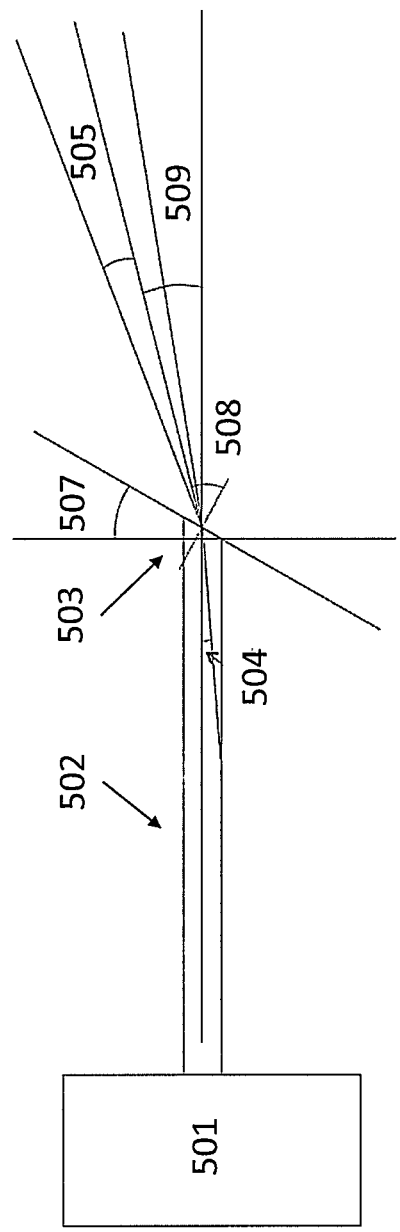
FIGS. 5A-5B illustrate an optical fiber coupled to a laser source in accordance with an embodiment of the present invention.

FIG. 5 is a diagram of an optical fiber coupled to a laser source, in accordance with an embodiment of the present invention. Similar to FIG. 4, laser source 501 emits laser (light) energy into optical fiber 502 for transmission into the operative region. Being an optical fiber, the conveyance of laser energy into and out of the optical fiber 502 contemplates two acceptance angles: (i) the angle required for light traveling down a multimode optical fiber to remain in the fiber (504), and (ii) the angle of the laser energy exiting the end of the fiber (505).

In contrast to FIG. 4, FIG. 5 specifically shows the effect of having a tilt angle 507 at the tip of the distal end 503 of optical fiber 502. The angle of refraction 508 of the interface may be computed using Snells' law and the index of refraction of the two medium. The effect of the tilted distal end 503 and the angle of refraction 508 produce an angle of deflection 509 from the axis of the optical fiber 502. The light will exit from the tilted end of the fiber provided that the sum of the tilt angle 507 and acceptance angle 505 do not exceed the critical angle 510.

Figure 5B:
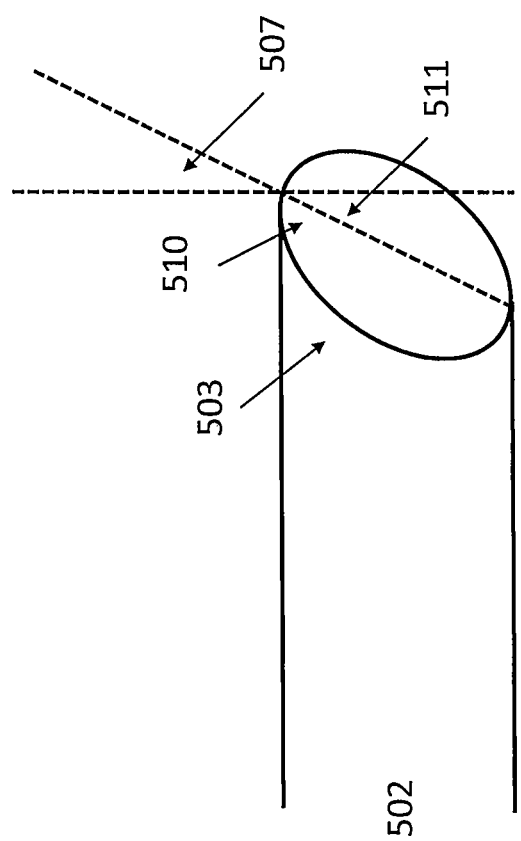

FIG. 5B illustrates the distal end 503 of optical fiber 502. As shown in FIG. 5B, the tip of the distal end 503 is formed by a non-orthogonal cut across the diameter of the optical fiber 502. The angle of the cut forms a non-right angle 510 with the length of the optical fiber. The adjacent angle 511 is identical to tilt angle 507 from FIG. 5A due to the rules of Euclidean geometry.

The preferred embodiments generally use laser light with a short absorption depth in water, i.e., an absorption depth less than 20 µm, which requires a corresponding absorption coefficient greater than 500 $cm^{-1}$. Accordingly, the preferred embodiments make use of light energy with either (i) a wavelength shorter than 200 nm or (ii) a wavelength longer than 2.8 µm. Among the options with wavelengths longer than 2.8 µm, light with wavelengths of 3 µm, 4.5 µm, 6 µm and 10 µm may be especially effective in certain embodiments. In particular, light with a wavelength of 3 µm may be advantageous because its absorption depth is very short and appropriate optical fibers are inexpensive. In contrast, optical fibers capable of conveying light energy of 4.5 µm, 6 µm, and 10 µm wavelength are more costly.

The preferred embodiments also make use of pulsed light energy. In some embodiments, the pulse width may be as long as 500 µs. Enhanced performance has been observed in embodiments that make use of pulse widths of 80 µs in length and shorter. Some embodiments make use of light energy with a pulse width of 60 µs.

FIG. 6 is a diagram of an optical fiber coupled to a laser source where a steam bubble may be deflected from the axis of the fiber by incorporating a fiber with tilted end and a laser source with high water absorption, in accordance with an embodiment of the present invention. The embodiment may be used to facilitate cataract surgery or any surgical application that involves cutting tissue. In some embodiments, the formation and collapse of the steam bubble may generate a directional shock wave.

The advantages of having a deflected steam bubble include (i) being able to reach locations that the tip of the optical fiber cannot reach, (ii) being able to deflect by rotation the fiber, (iii) being able to use the defection angle to add to mechanical bends of the optical fiber, and (iv) improving the surgeon's line of sight of the operative region and cutting process.

In FIG. 6A, optical fiber 601 conveys laser energy from laser source 602 to the tilted tip 603 at the distal end of the optical fiber 601. Tilted tip 603 is shaped to tilt angle 604. In FIG. 6A, tilt angle 604 is set to 20 degrees. Laser energy conveyed down the optical fiber 601 from the laser source 602 generates steam bubble 605. Steam bubble 605 is off-angle from the neutral axis of optical fiber 601, directed at a deflection angle 606. The combination of the tilted distal end 603 and the angle of refraction 607 produce the angle of deflection 606 from the axis of the optical fiber 601.

In FIG. 6B, optical fiber 601 may be subject to axial rotation 608 to form circular cutting path 609 with the deflected steam bubble 605. The circular cutting path 609 has the advantage of cutting holes with a larger diameter than fiber 601 itself.

FIG. 7 is a diagram of an optical fiber coupled to a laser source where a steam bubble may be deflected from the axis of the fiber by incorporating a fiber with a tilted end at 35 degrees, in accordance with an embodiment of the present invention. Similar to FIG. 6A, optical fiber 701 conveys laser energy from laser source 702 to tilted tip 703 at the distal end of optical fiber 701. Tilted tip 703 is shaped to a 35 degree tilt angle 704. Laser energy conveyed down optical fiber 701 from laser source 702 generates steam bubble 705. The effect of tilted distal end 703 and angle of refraction 707 produce an angle of deflection 706 from the axis of optical fiber 701.

With a tilt angle 704 of 35 degrees, the tip of steam bubble 705 extends out well beyond the diameter of the fiber 701. The deflection angle 706 allows the surgeon to cut the surface of the lens capsule while also keeping the fiber 701 parallel to the surface of the lens capsule, improving visibility of the operative region. This helps a surgeon see the location of the fiber tip 703 while cutting material below the fiber tip 703.

In FIG. 7B, optical fiber 701 may be subject to axial rotation 708 to form circular cutting path 709 using deflected steam bubble 705. As discussed earlier, the circular cutting path 709 has the advantage of cutting holes in the material with a larger diameter than the fiber 701 itself. Specifically, steam bubble 705 has a larger 35 degree tilt at its tip 703 that creates a larger circular cutting path 709 from the rotation of the optical fiber 701.

Figure 8A:
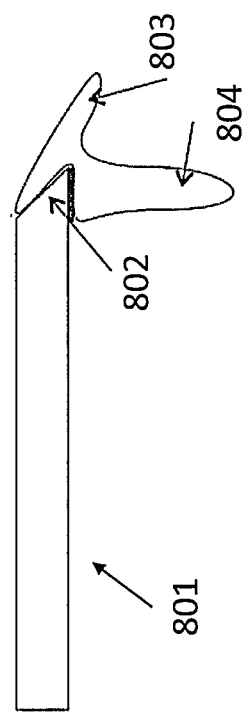
FIGS. 8A-8B illustrate an optical fiber with a tip with a tilt angle of 45 degrees, in accordance with an embodiment of the present invention.

FIG. 8 is a diagram of an optical fiber 801 with a tip 802 with a tilt angle of 45 degrees, in accordance with an embodiment of the present invention. In practice, some light exits the tilted tip 802 and some light exits the side of fiber 801 because the critical angle of fused silica is 44.6 degrees in air and slightly lower in water. The light in fiber 801 that is below the critical angle and is refracted through the tilted surface and the laser light forms a steam bubble 803 at tilted tip 802. The light in the fiber 801 that is above the critical angle is reflected off of the surface of tilted tip 802 and exits the side of the fiber 801. This reflected laser energy forms a steam bubble 804 directed out the side of the fiber 801. Thus steam bubbles 803, 804 are formed, both of which may be used to cut in two locations at once. By carefully selecting the angle of the tilted tip 802, the relative size and power of the steam bubbles 803, 804 can be controlled. In some embodiments, steam bubbles 803 and 804 may merge due to their close proximity to each other.

Figure 8B:
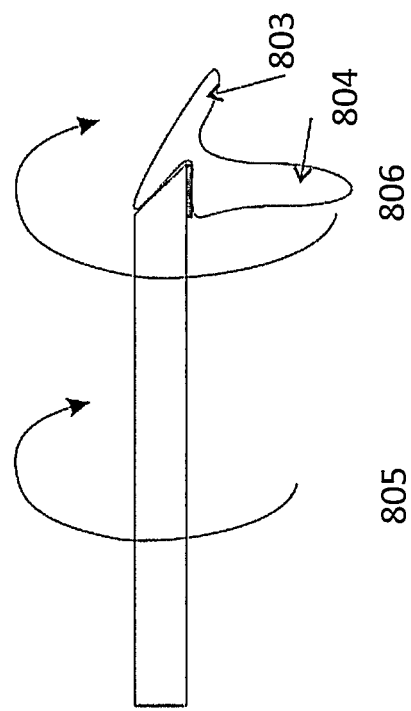

FIG. 8B is a diagram of optical fiber 801 with fiber rotation 805, in accordance with an embodiment of the present invention. Rotation 805 moves steam bubbles 803, 804 in a circular cutting path 806 around the fiber 801 to improve cutting and removal of targeted material. Although tilted tip 802 is 45 degrees, in other embodiments, a different angled tip may create a different circular cutting path in other embodiments.

Figure 9A:
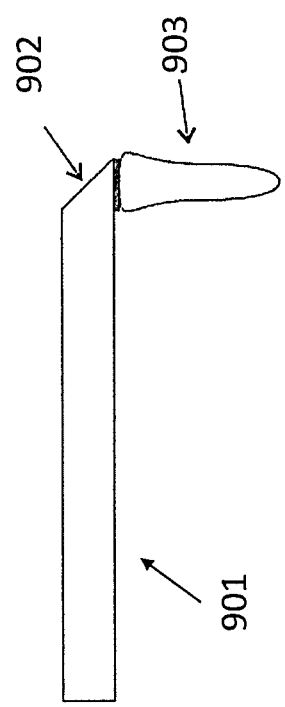
FIGS. 9A-9B illustrate an optical fiber with a tip with a tilt angle of 50 degrees, in accordance with an embodiment of the present invention.

FIG. 9 is a diagram of an optical fiber 901 with a tip 902 with a tilt angle of 50 degrees, in accordance with an embodiment of the present invention. In FIG. 9A, when surrounded by air or water, the tilt angle of tip 902 exceeds the critical angle. Thus, in both situations most of the light exits through the side of the fiber 901 due to internal reflection. Consequently, only a single steam bubble 903 is formed out the side of the fiber 901.

Figure 9B:
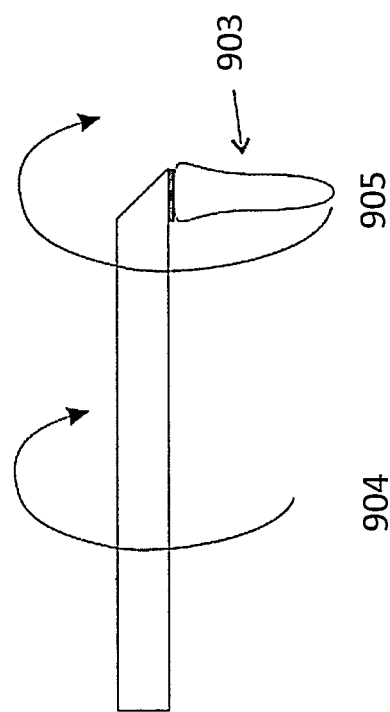

FIG. 9B is a diagram of optical fiber 901 with fiber rotation 904, in accordance with an embodiment of the present invention. Rotation 904 moves steam bubble 903 in a circular cutting path 905 around the fiber 901 to improve the cutting reach of the steam bubble 903.

In some embodiments, the size of the resulting steam bubbles may be altered by changing the input angle of the laser energy into the fiber. If the laser light is input into the fiber with a small divergence from the neutral axis of the fiber, laser light will tend to exit the end of the fiber. If the laser light is input into the fiber with a small divergence at an angle with respect the axis of the fiber, the light will tend to exit the side of the fiber.

FIG. 10 illustrates an embodiment of the present invention where the steam bubble is deflected from the axis of the fiber by incorporating a laser source with high water absorption (not shown), a bent optical fiber 1001, and a tilted tip 1002. In FIG. 10A, the deflection angle 1004 of the steam bubble 1003 may be added to the bend angle 1005 of the fiber 1001. The total angle of the steam bubble 1003 relative to the start of the fiber 1001 is the sum of the deflection angle 1004 and the fiber bend angle 1005. In some embodiments, the bend angle 1005 may be maintained by a bent tube around the bent optical fiber 1001.

FIG. 10B illustrates the use of bent optical fiber 1001 and tilted tip 1002 with a rotation 1006. With rotation 1006, the net deflection angle of the steam bubble 1003 may be modified from the sum of fiber bend angle 1005 and deflection angle 1004 to the net of the deflection angle 1004 subtracted from fiber bend angle 1005 by rotation of the fiber. In FIG. 10, the deflection angle 1004 is 20 degrees. Other embodiments may have different deflection angles and bend angles. Different angles create different circular cutting paths should the fiber be rotated. In some embodiments, where bent optical fiber 1001 is enclosed by a bent outer tube, a circular cutting path may be created by axially rotating the bent outer tube, which yields more net deflection angles and accesses more operative regions.

Figures 11A, 11B:
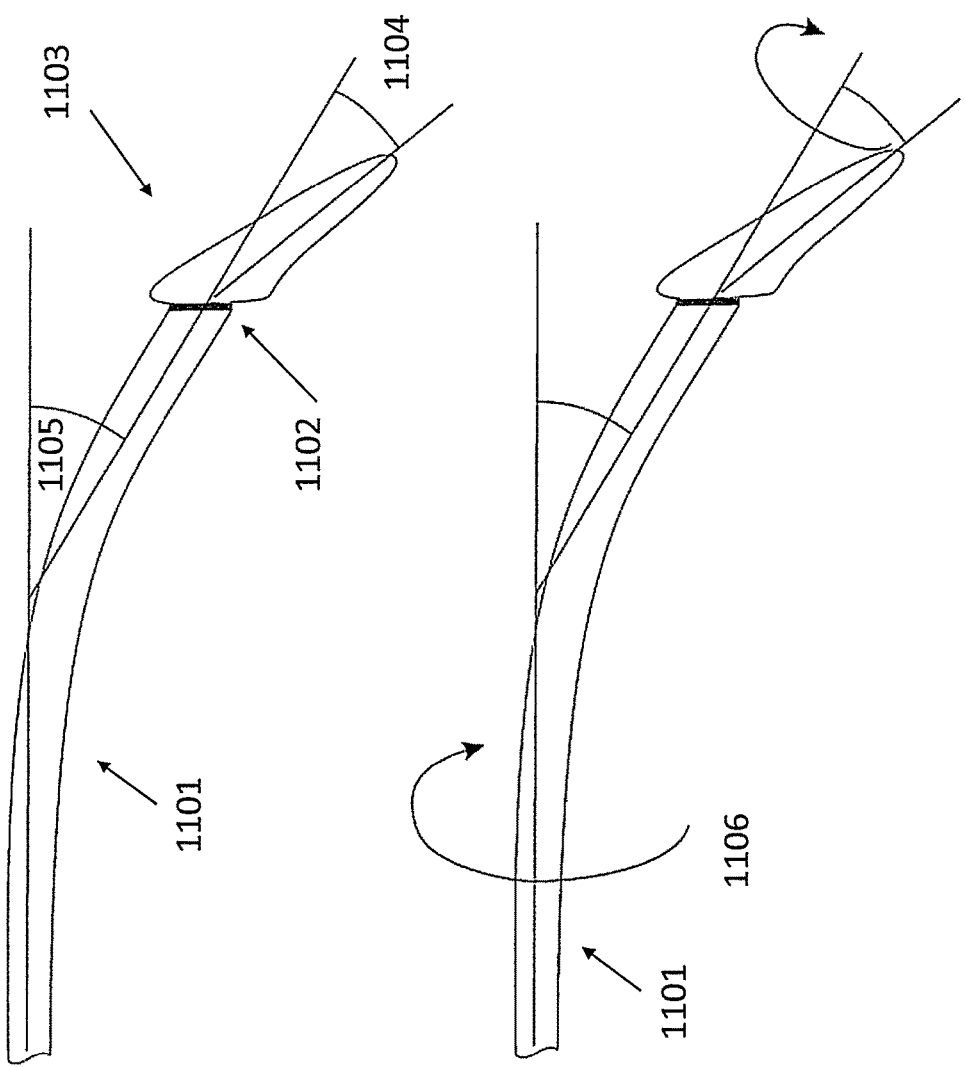
FIGS. 11A-11B illustrate an embodiment of the present invention where the steam bubble is deflected at an angle of 35 degrees from the axis of the fiber by incorporating a laser source with high water absorption, a bent optical fiber, and a tilted tip.

FIG. 11 illustrates an embodiment of the present invention where the steam bubble is deflected at an angle of 35 degrees from the axis of the fiber by incorporating a laser source with high water absorption (not shown), a bent optical fiber 1101, and a tilted tip 1102. Similar to FIG. 10A, in FIG. 11A, the deflection angle 1104 of the steam bubble 1103 is added to the bend angle 1105 of the fiber 1101. The total angle of the steam bubble 1103 relative to the start of the fiber 1101 is the sum of the deflection angle 1104 and the fiber bend angle 1105. In some embodiments, the bend angle 1105 may be maintained by a bent tube around the bent optical fiber 1101.

FIG. 11B illustrates the use of bent optical fiber 1101 and tilted tip 1102 with a rotation 1106. In FIG. 11B, the net deflection angle of the steam bubble 1103 may be modified by rotation of the fiber 1101. In some embodiments, where bent optical fiber 1101 is enclosed by a bent outer tube, a circular cutting path may be created by axially rotating the bent outer tube to yield even more net deflection angles and access different operative regions.

FIG. 12 illustrates an embodiment of the present invention where the steam bubble is deflected from the axis of the fiber by incorporating a laser source with high water absorption, a bent optical fiber, and a tilted end at the fiber. In FIG. 12A, because the tilt angle of the tip 1202 is less than the critical angle, steam bubbles 1203, 1206 are formed from both the tilted tip 1202 and the side of the tip of the fiber 1201. The deflection angle 1204 of the steam bubbles are added to the bend angle 1205 of the fiber 1201. Combined with bend angle 1205, the steam bubble 1206 may be directed behind the tip 1202. In some embodiments, this provides an advantage of being able to cut material behind corners or behind the tip 1202 of the fiber 1201. In some embodiments, the bend angle 1205 may be maintained by a bent tube around the bent optical fiber 1201.

FIG. 12B illustrates the use of fiber 1201 and tilted tip 1202 with rotation 1207. In FIG. 12B, the rotation 1207 of fiber 1201 produces cutting paths 1208 and 1209 in front of and along the side of the fiber due to the combination of the steam bubbles 1203 and 1206. These cutting paths have the advantage of removing a large volume of material in a single rotation. In some embodiments, where bent optical fiber 1201 is enclosed by a bent outer tube, a circular cutting path may be created by axially rotating the bent outer tube to yield even more net deflection angles and access different operative regions.

FIG. 13 illustrates an embodiment of the present invention where the resulting steam bubble exits from the side from a bent optical fiber with a tilted end at the fiber. In FIG. 13A, the tilt angle 1302 of the tip 1302 exceeds the critical angle, resulting in a steam bubble 1303 that exits from the side of the fiber 1301. In some embodiments, the bend angle 1304 may be maintained by a bent tube around the bent optical fiber 1301.

FIG. 13B illustrates the use of fiber 1301, tilted tip 1302, and steam bubble 1303 with rotation 1305, in accordance with an embodiment of the present invention. In this embodiment, rotation 1305, in combination with the bend angle 1304 and the length of the steam bubble 1303, produces a wide cutting path 1306. In some embodiments, where bent optical fiber 1301 is enclosed by a bent outer tube, a circular cutting path may be created by axially rotating the bent outer tube to yield even more net deflection angles and access different operative regions.

The bending of the fiber can be achieved by numerous methods, such as pre-bent glass fibers and fibers bent in an outer tube. In some embodiments, bend fibers may be dynamically controlled. In certain embodiments, those bend fibers may be dynamically bent in a robotically controlled tube mechanism. In other embodiments, the fibers may be bent by a robotically controlled flexure mechanism.

The present invention is not limited to embodiments using the aforementioned systems and the associated instrument drive mechanisms. One skilled in the art would appreciate modifications to facilitate coupling to different robotic arm configurations.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A surgical device comprising:
    an optical fiber having a proximal end, a distal end, and a neutral axis at the distal end,
    wherein the optical fiber is configured to generate a steam bubble from light energy conveyed out the distal end of the fiber, the proximal end is operatively connected to a light source, and the distal end comprises a tip with a tilted edge that is non-orthogonal and non-symmetrical with respect to the neutral axis, the light energy being conveyed out the tilted edge to generate the steam bubble off-angle from the neutral axis of the optical fiber,
    wherein the titled edge forms an angle such that at least a portion of the light energy (i) is incident on the tilted edge at an angle of incidence that is less than a critical angle and (ii) exits the optical fiber from the tilted edge.

2. The device of claim 1, further comprising a tube that encloses the optical fiber.

3. The device of claim 2, wherein the tube is pre-bent at a predetermined angle.

4. The device of claim 1, wherein an angle of the tilted edge exceeds 45 degrees.

5. The device of claim 1, wherein an angle of the tilted edge does not exceed 45 degrees.

6. The device of claim 5, wherein the angle of the tilted edge exceeds 7 degrees.

7. The device of claim 1, wherein the optical fiber is further configured to generate a second steam bubble from the application of the same laser energy conveyed out the tilted edge of the distal end of the fiber.

8. The device of claim 1, wherein the tilted edge of the tip of the distal end of the optical fiber extends across the entire diameter of the optical fiber.

9. The device of claim 1, wherein the tilted edge of the tip of the distal end of the optical fiber is flat across the entire diameter of the optical fiber.

10. A method comprising:
    transmitting light energy through an optical fiber;
    generating a steam bubble; and
    directing the steam bubble to an operative region of a patient;
    wherein the optical fiber has a proximal end, a distal end, and a neutral axis at the distal end, the distal end comprising a tip with a tilted edge that is non-orthogonal and non-symmetrical with respect to the neutral axis, the optical fiber being configured to generate the steam bubble from light energy conveyed out the tilted edge of the distal end of the fiber, the proximal end being operatively connected to a light source, and the steam bubble being generated off-angle from the neutral axis of the optical fiber,
    wherein the titled edge forms an angle such that at least a portion of the light energy (i) is incident on the tilted edge at an angle of incidence that is less than a critical angle and (ii) exits the optical fiber from the tilted edge.

11. The method of claim 10, wherein the optical fiber is enclosed within a tube.

12. The method of claim 11, wherein the tube is pre-bent at a predetermined angle.

13. The method of claim 11, further comprising axially rotating the tube to generate a circular cutting path for the steam bubble.

14. The method of claim 10, further comprising axially rotating the optical fiber to generate a circular cutting path for the steam bubble.

15. The method of claim 10, wherein an angle of the tilted edge exceeds 45 degrees.

16. The method of claim 10, wherein an angle of the tilted edge does not exceed 45 degrees.

17. The method of claim 16, wherein the angle of the tilted edge exceeds 7 degrees.

18. The method of claim 10, further comprising generating a second steam bubble from the application of the same laser energy conveyed out the tilted edge of the distal end of the fiber.

19. The method of claim 10, wherein the tilted edge of the tip of the distal end of the optical fiber extends across the entire diameter of the optical fiber.

20. The method of claim 10, wherein the tilted edge of the tip of the distal end of the optical fiber is flat across the entire diameter of the optical fiber.

\* \* \* \* \*